United States Patent [19]
Kitado et al.

[11] Patent Number: 5,167,610
[45] Date of Patent: Dec. 1, 1992

[54] SLEEP INDUCING SYSTEM

[75] Inventors: Masako Kitado; Izumi Mihara, both of Osaka, Japan

[73] Assignee: Matsushita Electric Works, Ltd., Japan

[21] Appl. No.: 534,657

[22] Filed: May 23, 1990

[30] Foreign Application Priority Data

May 25, 1989 [JP] Japan ................. 1-131904
Dec. 25, 1989 [JP] Japan ................. 1-335338
Mar. 27, 1990 [JP] Japan ................. 2-77805

[51] Int. Cl.⁵ ............................ A61M 21/00
[52] U.S. Cl. ............................ 600/026; 128/905
[58] Field of Search ................. 600/26–28; 128/905, 716–724

[56] References Cited

U.S. PATENT DOCUMENTS 3,576,185 4/1971 Schulz .................... 600/27
4,665,926 5/1987 Leuner et al. ............ 600/26

Primary Examiner—Lee S. Cohen
Assistant Examiner—John P. Lacyk
Attorney, Agent, or Firm—Leydig, Voit & Mayer

[57] ABSTRACT

A sleep inducing system is arranged to discriminate a proper time of falling asleep on the basis of respiration cycle detected as a biological signal, and to give to human body a sleep inducing stimulus in response to the discriminated proper time. Sleep induction can be thereby attained with respect to the human body organically and in a relatively short time.

5 Claims, 4 Drawing Sheets

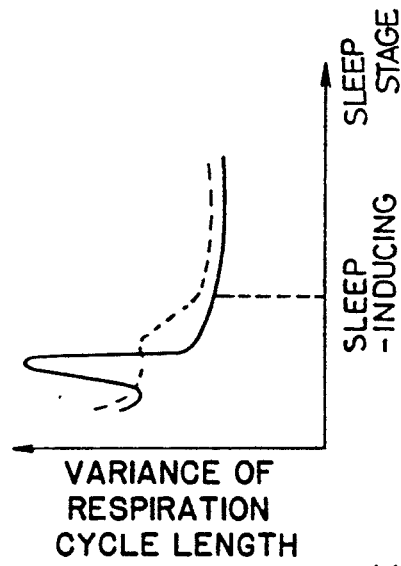
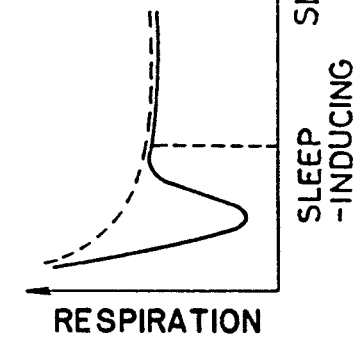
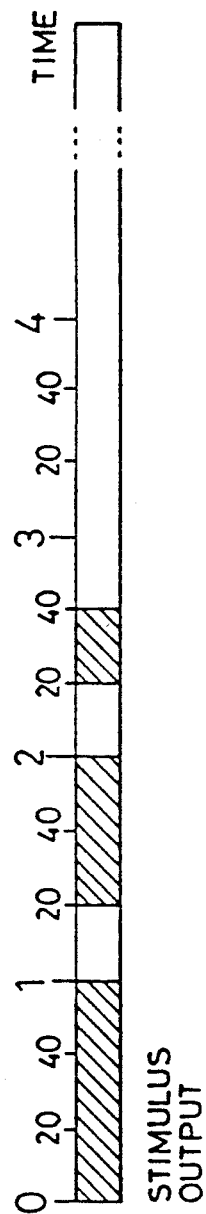

SLEEP INDUCING SYSTEM

BACKGROUND OF THE INVENTION

This invention relates to a sleep inducing system and, more particularly, to a system which detects respirations of human body as a biological signal and induces the human body effectively and organically on the basis of the detected respirations.

The sleep inducing system of the kind referred to is effectively utilizable in realizing a smooth falling asleep of a subject likely to become sleepless due to temporary or chronic excitement, mental stress or the like.

DESCRIPTION OF RELATED ART

In recent years, it has been a remarkable tendency that such mental stresses as anxiety, dissatisfaction, anger, irritation and so on develope rather oppressively as social complexity advances, and the stresses have been the cause for sleep disorders. Accordingly, various attempts have been made to remove the respective stresses to calm down mental state of the subject and to let the subject fall asleep. For this purpose, it is required to determine the mental state of the subject on the basis of biological signals obtained from the subject's human body, and to stabilize, for example, elevated mentality. For the biological signals, the ones originated from the subject's brain and heart may be utilized, but their detection requires that sensor electrodes are placed directly on the subject's body so that the subject may be rather annoyed by such sensor electrodes to be strained, and the detection has been much troublesome to be utilized for attaining the sleep induction.

As a measure for eliminating the stresses, on the other hand, it has been known to be effective to repetitively draw deep breath so as to attain mental calmness. Since such deep breath can be done through the subject's own mental control, this measure will be useful for promoting the subject's mental calmness. However, the respiration is carried out normally unconsciously, and there may arise a problem that a mere repetition of conscious respiration may happen to rather elevate the subject's level of consciousness, so as to render the measure to be not suitable for the sleep induction intended.

As other measures for employing organically the respiration as the biological signals, there have been disclosed in U.S. Pat. No. 3,576,185 of H. Schulz et al and U.S. Pat. No. 4,665,926 of H. Leuner et al, an induction of the subject's respiration rhythm to be of a tempo easy to fall asleep by means of voice and optical devices, and a provision of visual or auditory stimulus upon determination of relaxed state of the subject with inhalation, exhalation and pause of the respiration detected, while reducing muscular and brain activity for biological refreshment with the subject's body relaxed and rested, respectively. In the former case, it appears possible to promote the sleep by rendering the tempo of the subject's respiration to be that easy to fall asleep, but there has been involved a problem still in realizing the sleep induction organically and in a relatively short time. In particular, this measure has failed to detect the respiration rate and thus has not been suggestive to the idea of accurately discriminating biological state of the subject in view of the respiration rate for realizing a proper sleep induction. In the latter event, it appears that a highly relaxed state is attempted to be induced for the subject's muscle and brain and an action of refreshment is provided to the subject in view of the biological signals, but this measure still has not reached a technical level of accurately discriminating the biological state with the respiration utilized as a parameter for realizing the sleep induction organically in a relatively short time.

SUMMARY OF THE INVENTION

A primary object of the present invention is, therefore, to provide a sleep inducing system which employs the respiration as the biological signals for shifting the subject organically into the state of sleep in accordance with the respiration cycle, and is capable of realizing the sleep induction smoothly organically within a short time.

According to the present invention, this object can be attained by means of a sleep inducing system comprising means for detecting the subject's respiration as biological signals, means for discriminating a proper time for falling asleep with respiration cycle detected as a parameter by the detecting means, and a stimulus output means for providing to the subject's body a sleep inducing stimulus in response to an output from said discriminating means.

Other objects and advantages of the present invention shall be made clear in the following description of the invention detailed with reference to an embodiment of the present invention.

BRIEF DESCRIPTION OF THE DRAWINGS

FIG. 8 is a graph showing the relationship between the sleep stage and the respiration rate in the system of FIG. 1;

FIG. 9 is a graph showing the relationship between the sleep stage and the variance of respiration cycle length in the system of FIG. 1; and FIG. 10 is an explanatory diagram for another embodiment of the stimulus output in the system of FIG. 1.

Figure 1:
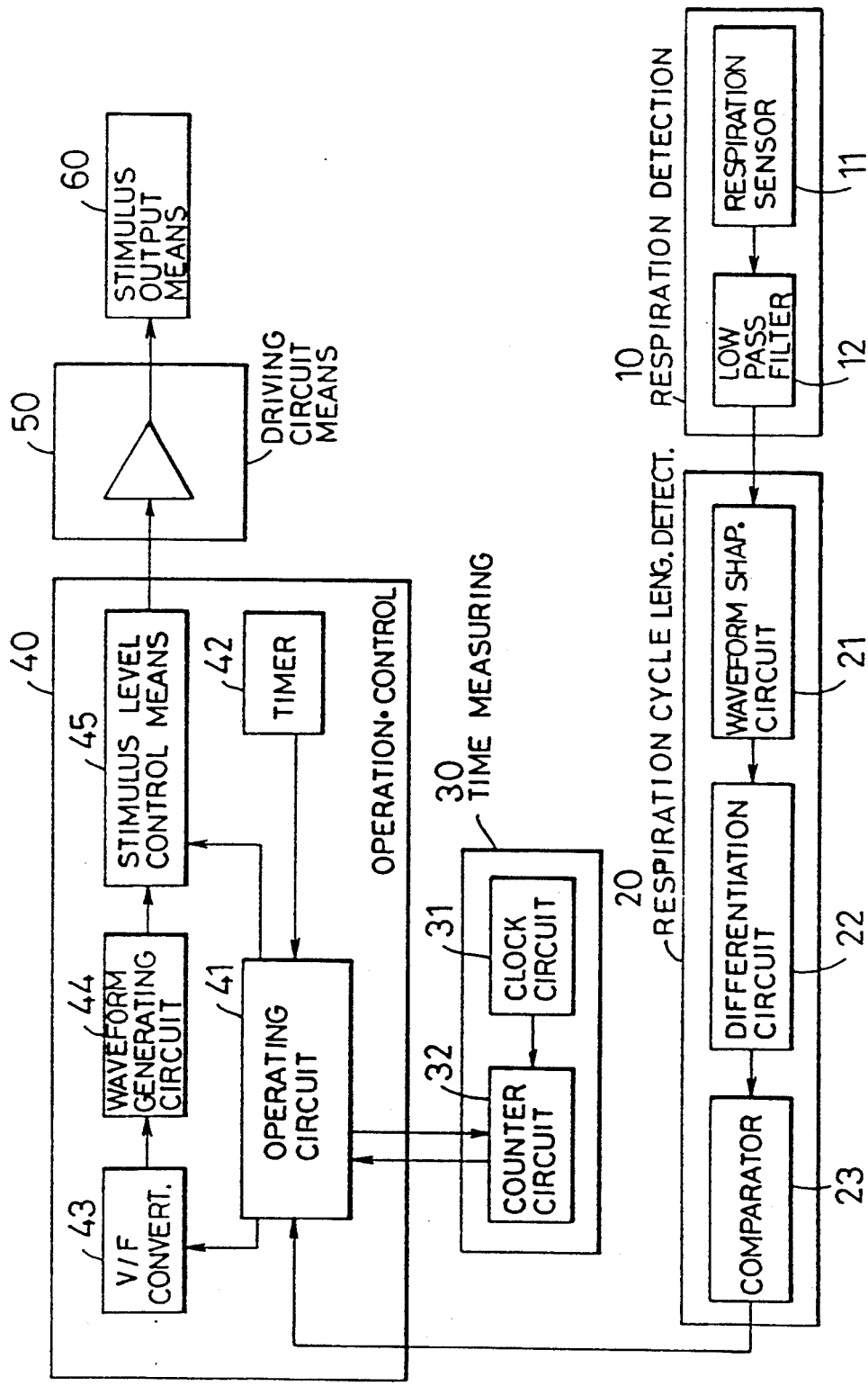
FIG. 1 is a block diagram of the sleep inducing system according to the present invention.

While the present invention shall now be explained in detail with reference to the embodiment shown in the drawings, it should be appreciated that the intention is not to limit the invention only to the embodiment shown but rather to include all modifications, alterations and equivalent arrangements possible within the scope of appended claims.

DETAILED DESCRIPTION OF THE PREFERRED EMBODIMENT

In FIG. 1, there is shown in a block diagram the sleep inducing system according to the present invention, which comprises a respiration detecting section 10, a respiration cycle length detecting section 20, a time measuring section 30 and an operation and control section 40 to which a stimulus output means 60 is connected through a driving circuit means 50.

Figure 2:
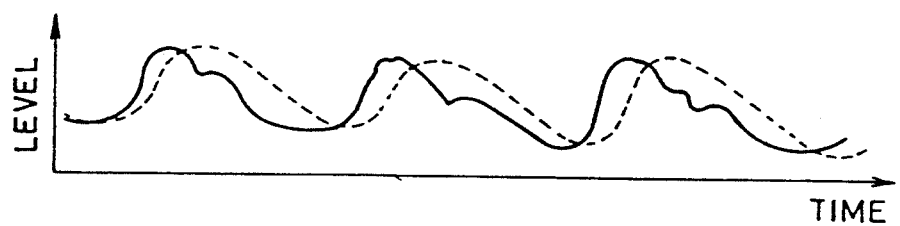
FIG. 2 is a graph showing the relationship of operating level of a low-pass filter with respect to time in the system of FIG. 1.

More specifically, the respiration detecting section 10 includes a respiration sensor 11 and a low-pass filter 12. The respiration sensor 11 is provided in a shape mountable to the subject's abdominal or chest region without substantial feeling of foreign matter or unpleasantness for detecting variation in the region's bulgeness by means of a strain gauge or the like. For the detection, a bed sheet type strain gauge, a thermistor type sensor disposed in a zone where nose exhalation is sensible enough for detecting thermal change or the like means may also be employed. The low-pass filter 12 is to allow only lower frequency component below about 2 Hz and to cut any other noise than the respiration or any minor sensor output so that output signals from the respiration detecting section 10 will be shaped, as shown in FIG. 2, from such solid line curve to such dashed line curve as shown in FIG. 2, upon which an average output value denoted by the dashed line curve is made to be at a delayed phase with respect to an average detection value denoted by the solid line curve. That is, the low-pass filter 12 also functions as a phase delay means in addition to the primarily expected function.

The respiration cycle length detecting section 20 comprises a waveform shaping circuit 21, a differentiation circuit 22 and a comparator 23, in which the waveform shaping circuit 21 amplifies the output signal of the low-pass filter 12 in the respiration detecting section 10 and shapes it into a rectangular wave which is provided to the differentiation circuit 22, rises and falls only of the rectangular wave are detected at the differentiation circuit 22, positive or negative outputs corresponding to the rise or fall only from the differentiation circuit 22 is compared at the comparator 23 with a predetermined reference level, and a pulse is provided out of the comparator 23 for every cycle of the respiration. It should be appreciated here that the respiration cycle length detecting section 20 may be of any other arrangement so long as the arrangement is the one which provides the pulse for every respiration cycle.

The time measuring section 30 comprises a clock circuit 31 and a counter circuit 32, wherein the counter circuit 32 is arranged to be reset by an output from an operating circuit 41 later described of the operation and control section 40 and to increase one count for every input clock wave from the clock circuit 31, and such output of the counter circuit 32 is provided to the operating circuit 41 of the operation and control section 40 along with the output of the comparator 23 in the respiration cycle length detecting section 20.

The operation and control section 40 comprises, in addition to the operating circuit 41, a timer circuit 42, a voltage/frequency converter 43, a waveform generating circuit 44 and a stimulus level control means 45. The operating circuit 41 has a memory function and an operating function, and calculates the average or variance value of a plurality of the respiration cycle length to set a stimulus level gradually decreasing as time goes by. When, in this case, the pulse from the comparator 23 is received by the operating circuit 41 and after reading the count from the counter circuit 32 at this circuit 41, the operating circuit 41 resets the counter circuit 32. When the counter circuit 32 receives from the operating circuit 41 the reset signal, the count of the counter circuit 32 is returned to zero. The operating circuit 41 is also receiving from the timer 42 a clock signal at every interval of 20 to 30 seconds, and calculates the average value of five or six respiration cycles stored, from the one immediately before the time at which the clock signal is provided to the operating circuit 41.

Figure 6:
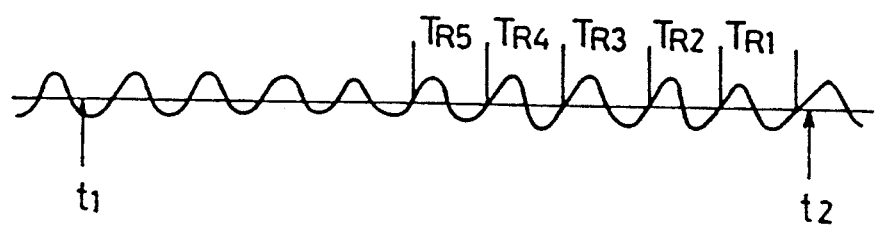
FIG. 6 is a graph showing the relationship between variance in respiration cycle length and time elapsed in the system of FIG. 1.

Referring more specifically to the above also with reference to FIG. 6, it is assumed here that the clock signal is provided out of the timer 42 at the time t1 and t2. Now, as the clock signal is provided from the timer 42 to the operating circuit 41 at the time t2, the operating circuit 41 reads out of its memory five stored respiration cycles $T_{R1}$ to $T_{R5}$ detected prior to the time t2 and including the one immediately before the time t2, and calculates their average value $T_{AD}(t2) = (T_{R1} + T_{R2} + T_{R3} + T_{R4} + T_{R5})/5$ (for initial period of about 30 to 60 seconds, since the respiration cannot be detected, a standard respiration cycle length calculated in view of preliminary stored data is to be provided). Here, an output corresponding in particular to a cycle length 0.9 to 1.2 times as large as the average respiration cycle length $T_{AV}$ is provided from the operating circuit 41 to the voltage/frequency converter 43 to determine a cycle length T of the stimulus given to the subject's body as will be detailed later, and this cycle length T is maintained until a next clock signal is received from the timer circuit 42. The waveform generating circuit 44 is made, at this cycle length T provided from the voltage/frequency converter 43, to generate a sinusoidal wave or either half-wave rectified or blunted wave of the sinusoidal wave or a waveform closely resembling the respiration cycle, and this waveform is provided to the stimulus level control means 45, where the stimulus level is so set as to be gradually lowered as time elapses. In this case, the arrangement may be so made as to detect the time elapsed by counting at the operating circuit 41 the number of the clock signals received from the timer circuit 42, or to determine that the subject has fallen asleep deeply and corresponding time has elapsed, upon decrement in the variance of the respiration cycle length calculated at the operating circuit 41, and to lower the stimulus level.

As has been referred to, the level of the stimulus given to the subject is controlled at the stimulus level control means 45, thus controlled level of the stimulus is amplified at an amplifier in the driving circuit means 50 and a driving power for the stimulus output means 60 is provided from the driving circuit means 50. The stimulus output means 60 employs, for example, a light emitting means, and the amplifier in the driving circuit means 50 may comprise a transistor, thyristor or the like which can control a power supply rate to the light emitting means in accordance with the output of the stimulus level control means 45.

Figure 3:
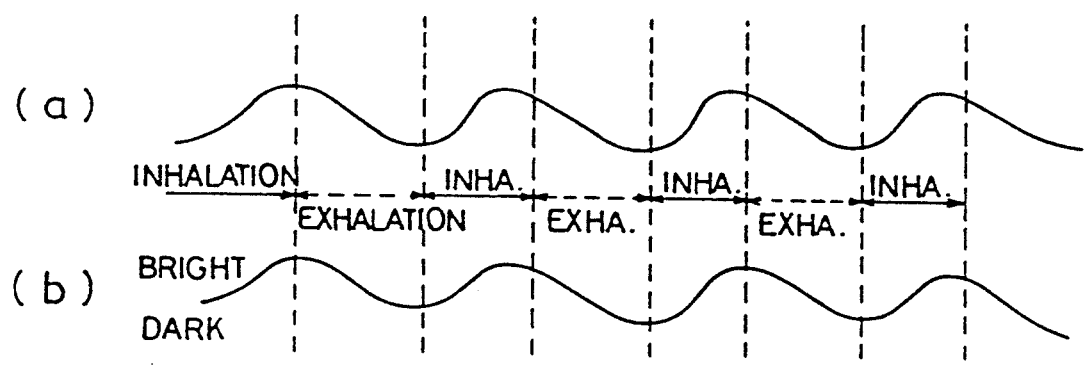
FIG. 3 is a graph showing the relationship between the respiratory rhythm and the brightness of light emitted as a stimulus output in the system of FIG. 1.
Figure 4:
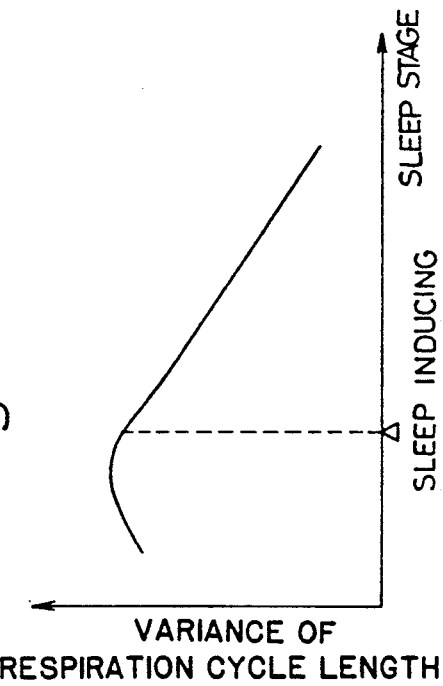
FIG. 4 is a graph showing the temporal variation of the emitted light brightness in the system of FIG. 1.

Next, the operation of the sleep inducing system according to the present invention shall be explained in relation to the human body. As has been briefly referred to already, it is known that the settling of the respiration rhythm is effective to reduce the mental stress and to attain mental relaxation. In awakening state, the respiration rate varies in conformity to the decrement in the awakening degree. As shown in FIG. 3, for example, the brightness of the light emitted by the stimulus output means 60 is caused to vary to be bright and dark during the awakening period in conformity to the respiration rhythm, so that the brightness will be gradually elevated upon the inhalation but will be gradually lowered upon the exhalation, whereby the emitted light brightness is controlled to be at delayed phase from real time of the inhalation or exhalation in accordance with the output of the low-pass filter 12, during the awakening period. Relative brightness of such light stimulus is so controlled as to be gradually lowered to become darker as time lapses. Further, it is preferable that, as shown in FIG. 4, an open loop control is carried out for gradually darkening with time up to a time when a detection of the respiration rhythm can be discriminated to be an indication of a state in which the subject has fallen asleep, and then a feedback control is carried out for providing the light stimulus as adapted to the deepness of the sleep immediately after the discrimination of the fallen-asleep state, so that the subject's environment will be made darker as the sleep becomes deeper.

Figure 5:
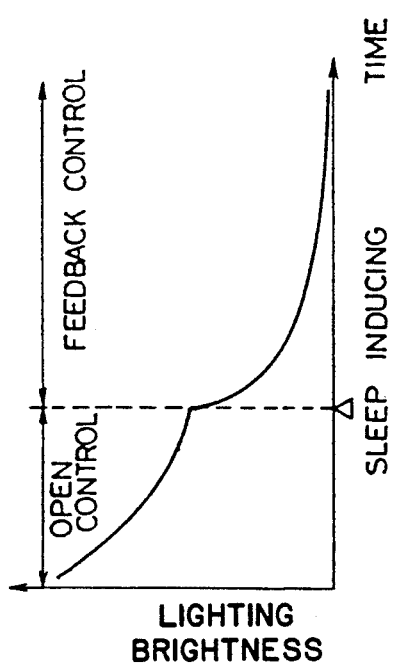
FIG. 5 is a graph showing the relationship between sleep stage and variance in respiration cycle length in the system of FIG. 1.

The discrimination whether or not the subject has fallen asleep is carried out preferably in the relationship between the variance of the respiration cycle length and the sleeping depth. It has been discovered through studies made by the present inventors that, as shown in FIG. 5, the variance of respiration cycle length becomes slightly larger immediately before the falling asleep but gradually smaller as the sleep becomes deeper, and thus the discrimination can be achieved by calculating the variance of respiration cycle length. With results of such calculation utilized, it is possible to set switch-over time from the open loop control to the feedback control. Further, with the low-pass filter 12 employed, the output of the stimulus output means 60 can be delayed in phase with respect to the detected respiration, so that the light stimulus will not be caused to abruptly vary in the brightness immediately after the peaks of the inhalation and exhalation and the peak to peak time difference between the brightening phase and darkening phase will be made smaller so as to prevent the brightness from being abruptly varied and not to cause the awakening degree of the subject to be rather elevated. That is, the sleep induction can be quickly carried out, following natural rhythm of the respiration.

In a more practical aspect, the light is dimmed in every period of 20-30 seconds in conformity to the average value of the variance of respiration cycle length occurring in accordance with the decrement in the awakening degree, the respiration is consequently made regular to have the proper time for falling asleep in the relaxed state reached gradually, and the subject is induced into the sleeping state which is deep even from the time of falling asleep. The light dimming is controlled in the amplitude by the stimulus level control means 45 so as to be exponentially faded out, and the light stimulus is to be given at a constant cycle for a period of 20-30 seconds since the variance of respiration cycle length is remarkably decreased as the sleep becomes deeper, whereby a more excellent matching can be attained between the light stimulus cycle and the respiration cycle. The detection of the average respiration cycle length at every period of 20 to 30 seconds is for the purpose of rendering the system to be correspond to such physiological phenomenon that in the human sleep just at the time of falling asleep, the depth of sleep is not stable and often varies at such period as above. It has been also found that the average value and variance value of the respiration rate during the sleep are decreased in contrast to those during the awakening, due to that the stimulus output is provided at the slightly delayed phase with respect to the average value of the respiration cycle length, and, accordingly, it is made easier to induce the human body into a deeper state of sleep.

Figure 7:
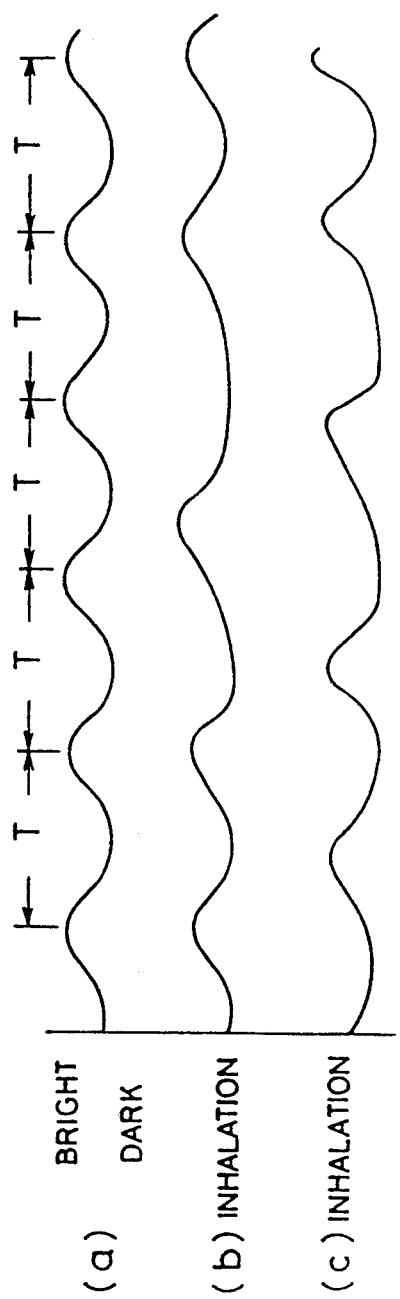
FIG. 7 is a graph showing the relationship between the cycle of stimulus output to the emitted light brightness and the measured respiratory cycle in the system of FIG. 1.

Assuming now that the light stimulus is carried out for 20-30 seconds with the repetition of the bright and dark conditions at a cycle length T about 0.9-1.2 times as large as the average respiration cycle length, as shown by a waveform (a) in FIG. 7, and that initially the inhalation takes place under the bright condition, the respiration cycle which has even large cycle length variance from the time when the awakening degree is high to the time immediately before the falling asleep so as to be out of phase with the stimulus light cycle will be made to restore the initial state of carrying out the inhalation under the bright condition (see a waveform (b) in FIG. 7). In an event where the inhalation takes place under the dark condition initially, on the other hand, the respiration can be so induced gradually as to carry out the inhalation under the bright condition and be thus settled to be regular, and the falling asleep is reached (see a waveform (c) in FIG. 7). Depending on the individual subject, there is a case in which the inhalation takes place under the dark condition in the initial state and, in which event, the operation may be carried out in opposite manner to the above.

According to another feature of the present invention, further, a plurality of falling-asleep pattern are taken into consideration, and the discrimination of the proper time for falling asleep at which the subject can easily fall asleep is made to be reliable. Typically, there exist two patterns, in first of which the respiration rate gradually decreases until the sleep becomes deep to a certain level and thereafter maintains substantially a constant level, as shown by a dashed line curve in FIG. 8, and in second of which the respiration rate extremely decreases once immediately before the falling asleep and thereafter increases again to show a stable level, as shown by a solid line curve in FIG. 8. In respect of the variance of respiration cycle length, there are also a first pattern in which the variance gradually decreases until the sleep becomes deep to a certain level as shown by a dashed line curve in FIG. 9, and a second pattern in which the variance abruptly increases once immediately before the falling asleep but thereafter quickly decreases to show substantially a constant level as shown by a solid line curve in FIG. 9. While the first pattern of the respiration rate represented by the dashed line curve in FIG. 8 has been generally known, the second respiration rate pattern of the solid line curve in FIG. 8 as well as the first and second variance patterns of the dashed and solid line curves in FIG. 9 are the discovery through eager development made by the present inventors for improving the reliability of the discrimination of the sleep state and the sleep induction. Accordingly, the operating circuit 41 are so arranged as to operate both of the first and second patterns, to monitor the respiration data and to make the discrimination of the falling asleep upon detecting either one of the first and second patterns, so as to prosecute such predetermined operation as has been referred to. With this arrangement, the time when the subject has fallen asleep can be discriminated with a high reliability.

According to still another feature of the present invention, a stimulus of a fixed cycle length is given in addition to the foregoing stimulus of the predetermined cycle length using the respiration data, so that these stimuli will be given to the subject alternately as repeated for several times, and a more organic sleep induction can be achieved. In this case, the clock signals of the timer circuit 42 in the operation and control section 40 are provided to the operating circuit 41 at predetermined intervals of, for example, two or three times of unit time (20–30 seconds) at initial stage of the stimulus provision but every unit time when the clock signals are generated after elapsing of several minutes as shown by arrows in FIG. 10. In calculating the average value $T_{Al}$ with respect to the five respiration cycle length $T_{R1}$ to $T_{R5}$ read out of the memory, since the respiration is made not detectable for initial 30–60 seconds, the stimulus of a fixed cycle length is given in this period. The same fixed cycle length stimulus is also given for following predetermined period as shown in FIG. 10, for example, for 40 seconds after 20 seconds from the termination of the initial 30–60 seconds or for a subsequent period of 20 seconds after 20 seconds from the termination of the second fixed stimulus period and so on. In providing the fixed cycle length stimulus, the operation at the operating circuit 41 is carried out on the basis of the preliminarily stored respiration cycle length (of, for example, about 4.5 to 6 sec.). Other arrangements are the same as those in the first feature.

According to the present feature, in particular, the first stimulus conforming to the cycle slightly longer than the normal respiration and the second stimulus conforming to the average respiration cycle length are provided alternately for several times as repeated at the predetermined intervals, whereby the subject is rendered to be able to respire naturally comfortably so as to become mentally calm similarly to the state after drawing deep respiration, the relaxation effect can be further elevated and an effectively faster sleep induction can be realized.

While in the above the stimulus has been described as being of light, the stimulus may be any of sound, vibration, wind, fragrance and the like, in which event the stimulus by means of the sound, vibration, wind or the like is to be generated at a predetermined frequency and its envelope is to be subjected to an amplitude-modification at a cycle length close to the average respiration cycle.

What is claimed is:

1. A sleep inducing system comprising:
   means for detecting a person's respiration and for providing the detected respiration sequentially as a biological signal;
   means receiving the biological signal for extracting therefrom a respiration cycle length and for providing an output signal indicative of the respiration cycle length;
   means receiving the output signal for determining therefrom a time when the person falls asleep on the basis of the respiration cycle length and for providing a second output signal indicative of the time of falling asleep, said means for determining the time of falling asleep upon detection of one of a first pattern in which the person's respiration gradually decreases in rate and a second pattern in which the person's respiration decreases in rate once abruptly and thereafter increases and becomes stable; and
   stimulus output means connected to said means for determining for varying a sleep inducing stimulus in response to the second output signal indicative of the time of falling asleep.

2. The system of claim 1 wherein said stimulus output means alternatingly provides at predetermined intervals the sleep inducing stimulus in a predetermined cycle length based on the respiration cycle length and at a constant cycle length.

3. A sleep inducing system comprising:
   means for detecting a person's respiration and for providing the detected respiration sequentially as a biological signal;
   means receiving the biological signal for extracting therefrom a respiration cycle length and for providing an output signal indicative of the respiration cycle length;
   means receiving the output signal for determining therefrom at a time when the person falls asleep on the basis of the respiration cycle length and for providing a second output signal indicative of the time of falling asleep, said means for determining including means for calculating variance of the respiration cycle length and determining the time of falling asleep upon detection of one of a first patter in which the variance of the respiration cycle length gradually decreases and a second pattern in which the variance of the respiration cycle length increases once abruptly and thereafter decreases and becomes stable; and
   stimulus output means connected to said means for determining for varying a sleep inducing stimulus in response to the second output signal indicative of the time of falling asleep.

4. The system of claim 3 wherein said stimulus output means alternatingly provides at predetermined intervals the sleep inducing stimulus in a predetermined cycle length based on the respiration cycle length and at a constant cycle length.

5. A sleep inducing system comprising:
   detecting means for detecting a person's respiration cycle length and for outputting a first signal corresponding to the detected respiration cycle length;
   determining means receiving the first signal for analyzing the first signal and thereby determining a time when the person falls asleep and for outputting a second signal indicative of the time of falling asleep; and
   a stimulus output means for applying a sleep inducing stimulus to the person and for altering the sleep inducing stimulus in response to he second signal.

* * * * *